(12) United States Patent
Quake et al.

(10) Patent No.: US 11,859,171 B2
(45) Date of Patent: Jan. 2, 2024

(54) METHOD FOR GENERATING EXTENDED SEQUENCE READS

(71) Applicant: Agency for Science, Technology and Research, Singapore (SG)

(72) Inventors: Stephen R. Quake, Stanford, CA (US); William F. Burkholder, Singapore (SG); Lewis Z. Hong, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 240 days.

(21) Appl. No.: 14/784,605

(22) PCT Filed: Apr. 17, 2014

(86) PCT No.: PCT/SG2014/000172
§ 371 (c)(1),
(2) Date: Oct. 15, 2015

(87) PCT Pub. No.: WO2014/171898
PCT Pub. Date: Oct. 23, 2014

(65) Prior Publication Data
US 2016/0076023 A1 Mar. 17, 2016

(30) Foreign Application Priority Data
Apr. 17, 2013 (SG) ............... 201302940-0

(51) Int. Cl.
*C12Q 1/68* (2018.01)
*C12N 15/10* (2006.01)
*C12Q 1/6869* (2018.01)

(52) U.S. Cl.
CPC ....... *C12N 15/1065* (2013.01); *C12Q 1/6869* (2013.01)

(58) Field of Classification Search
None
See application file for complete search history.

(56) References Cited

U.S. PATENT DOCUMENTS

| | | |
|---|---|---|
| 5,476,930 A | 12/1995 | Letsinger et al. |
| 5,780,613 A | 7/1998 | Letsinger et al. |
| 7,115,400 B1 | 10/2006 | Adessi et al. |
| 7,315,019 B2 | 1/2008 | Turner et al. |
| 7,582,420 B2 | 9/2009 | Oliphant et al. |
| 7,901,891 B2 | 3/2011 | Drmanac |
| 7,955,794 B2 | 6/2011 | Shen et al. |
| 8,003,354 B2 | 8/2011 | Shen et al. |
| 8,298,767 B2 | 10/2012 | Brenner et al. |
| 8,563,274 B2 | 10/2013 | Brenner et al. |
| 8,603,749 B2 | 12/2013 | Gillevet |
| 8,652,779 B2 | 2/2014 | Turner et al. |
| 8,653,779 B2 | 2/2014 | Yashiro et al. |
| 8,673,562 B2 | 3/2014 | Drmanac |
| 8,679,756 B1 | 3/2014 | Brenner et al. |
| 8,765,375 B2 | 7/2014 | Drmanac |
| 8,765,379 B2 | 7/2014 | Drmanac |
| 8,765,382 B2 | 7/2014 | Drmanac |
| 8,771,957 B2 | 7/2014 | Drmanac |
| 8,771,958 B2 | 7/2014 | Drmanac |
| 8,829,171 B2 | 9/2014 | Steemers et al. |
| 8,835,358 B2 | 9/2014 | Fodor et al. |
| 8,932,812 B2 | 1/2015 | Hogers et al. |
| 9,023,769 B2 | 5/2015 | Drmanac et al. |
| 9,034,580 B2 | 5/2015 | Cantor |
| 9,074,242 B2 | 7/2015 | Larson et al. |
| 9,085,798 B2 | 7/2015 | Chee |
| 9,102,980 B2 | 8/2015 | Brenner et al. |
| 9,127,307 B2 | 9/2015 | Adler, Jr. et al. |
| 9,150,852 B2 * | 10/2015 | Samuels ............ C12N 15/1075 |
| 9,260,753 B2 | 2/2016 | Xie et al. |
| 9,290,809 B2 | 3/2016 | Fodor et al. |

(Continued)

FOREIGN PATENT DOCUMENTS

| | | |
|---|---|---|
| AU | 2011274090 A1 | 2/2013 |
| EP | 2463386 A1 | 6/2012 |

(Continued)

OTHER PUBLICATIONS

Costea, PI., et al. TagGD: Fast and accurate software for DNA tag generation and demultiplexing, PLoS One, vol. 8(3), p. 1-5, Mar. 2013.*
Nelson JR., et al. Templiphi Ø29 DNA polymerase based rolling circle amplification of templates for DNA sequencing. .Bio Techniques, vol. 32, p. S44-S47, 2002.*
Extended European Search Report for European Application No. 14785836.9 dated Nov. 10, 2016.
Asan et al., "Paired-end sequencing of long-range DNA fragments for de novo assembly of large, complex mammalian genomes by direct intra-molecule ligation". PLoS One. 2012;7(9):e46211. doi: 10.1371/journal.pone.0046211.

(Continued)

*Primary Examiner* — Suryaprabha Chunduru
(74) *Attorney, Agent, or Firm* — COOLEY LLP; Heidi A. Erlacher; Edith Hang Yu Cheng (57) ABSTRACT

The present invention provides an approach to increase the effective read length of commercially available sequencing platforms to several kilobases and be broadly applied to obtain long sequence reads from mixed template populations. A method for generating extended sequence reads of long DNA molecules in a sample, comprising the steps of: assigning a specific barcode sequence to each template DNA molecule in a sample to obtain barcode-tagged molecules; amplifying the barcode-tagged molecules to obtain barcode-containing fragments; juxtaposing the barcode-containing fragments to random short segments of the original DNA template molecule during the process of generating a sequencing library to obtain demultiplexed reads; and assembling the demultiplexed reads to obtain extended sequence reads for each DNA template molecule, is disclosed.

23 Claims, 6 Drawing Sheets

(56) References Cited

U.S. PATENT DOCUMENTS

| | | | |
|---|---|---|---|
| 9,315,857 B2 | 4/2016 | Fu et al. | |
| 9,404,156 B2 | 8/2016 | Hicks et al. | |
| 9,453,262 B2 | 9/2016 | Gillevet | |
| 9,476,095 B2 | 10/2016 | Vogelstein et al. | |
| 9,514,272 B2 | 12/2016 | Kermani et al. | |
| 9,524,369 B2 | 12/2016 | Drmanac et al. | |
| 9,567,645 B2 | 2/2017 | Fan et al. | |
| 9,574,230 B2 | 2/2017 | Van et al. | |
| 9,637,785 B2 | 5/2017 | Drmanac | |
| 10,233,490 B2 | 3/2019 | Stapleton et al. | |
| 10,240,197 B1 | 3/2019 | Brenner et al. | |
| 10,246,744 B2 | 4/2019 | Vijayan et al. | |
| 10,273,541 B2 | 4/2019 | Hindson et al. | |
| 10,428,368 B2 | 10/2019 | Schildkraut et al. | |
| 10,731,141 B2 | 8/2020 | Iyidogan | |
| 11,255,847 B2 | 2/2022 | Belhocine et al. | |
| 2002/0190663 A1 | 12/2002 | Rasmussen | |
| 2006/0068415 A1* | 3/2006 | Jones | C12Q 1/6809 435/6.1 |
| 2009/0029385 A1 | 1/2009 | Christians et al. | |
| 2009/0105094 A1* | 4/2009 | Heiner | C12Q 1/6869 506/26 |
| 2010/0227329 A1 | 9/2010 | Cuppens | |
| 2011/0009294 A1* | 1/2011 | Jones | C12Q 1/6809 506/16 |
| 2012/0190663 A1 | 7/2012 | Gornik et al. | |
| 2012/0196754 A1 | 8/2012 | Quake et al. | |
| 2012/0270214 A1 | 10/2012 | Bernitz et al. | |
| 2012/0283145 A1 | 11/2012 | Wang | |
| 2013/0054151 A1 | 2/2013 | Kermani et al. | |
| 2013/0157870 A1 | 6/2013 | Pushkarev et al. | |
| 2013/0203634 A1 | 8/2013 | Jovanovich et al. | |
| 2013/0224751 A1 | 8/2013 | Olson et al. | |
| 2013/0237432 A1 | 9/2013 | Li et al. | |
| 2014/0018246 A1 | 1/2014 | Drmanac | |
| 2014/0034497 A1 | 2/2014 | Davis et al. | |
| 2014/0134614 A1 | 5/2014 | Dong et al. | |
| 2014/0214391 A1 | 7/2014 | Cope | |
| 2014/0256568 A1 | 9/2014 | Link | |
| 2015/0057163 A1 | 2/2015 | Rotem et al. | |
| 2015/0057947 A1 | 2/2015 | Drmanac et al. | |
| 2015/0087535 A1 | 3/2015 | Patel | |
| 2015/0094961 A1 | 4/2015 | Kermani et al. | |
| 2015/0148239 A1 | 5/2015 | Peter et al. | |
| 2015/0259674 A1 | 9/2015 | Steelman et al. | |
| 2016/0026758 A1 | 1/2016 | Jabara et al. | |
| 2016/0040228 A1 | 2/2016 | De Wit et al. | |
| 2016/0046985 A1* | 2/2016 | Drmanac | C12Q 1/6806 506/4 |
| 2016/0108394 A1 | 4/2016 | Lok | |
| 2016/0152972 A1 | 6/2016 | Stapleton et al. | |
| 2017/0009274 A1 | 1/2017 | Abate et al. | |
| 2019/0276884 A1 | 9/2019 | Stapleton et al. | |
| 2020/0231964 A1 | 7/2020 | Ben-Yehezkel et al. | |
| 2022/0275437 A1 | 9/2022 | Stapleton et al. | |

FOREIGN PATENT DOCUMENTS

| | | | | |
|---|---|---|---|---|
| EP | 2599877 A1 | 6/2013 | | |
| WO | WO 2004/070005 A2 | 8/2004 | | |
| WO | WO 2007/010252 A1 | 1/2007 | | |
| WO | WO 2008/076406 A2 | 6/2008 | | |
| WO | WO-2010048605 A1 * | 4/2010 | | C12N 9/1252 |
| WO | WO 2011/074960 A1 | 6/2011 | | |
| WO | WO 2011/143231 A2 | 11/2011 | | |
| WO | WO-2011143231 A2 * | 11/2011 | | C12N 15/1027 |
| WO | WO 2012/000445 A1 | 1/2012 | | |
| WO | WO 2012/061832 A1 | 5/2012 | | |
| WO | WO-2012061832 A1 * | 5/2012 | | C12N 15/1065 |
| WO | WO 2012/103154 A1 | 8/2012 | | |
| WO | WO 2012/149042 A2 | 11/2012 | | |
| WO | WO 2013/036929 A1 | 3/2013 | | |
| WO | WO 2014/071361 A1 | 5/2014 | | |
| WO | WO 2014/145820 A2 | 9/2014 | | |
| WO | WO-2014201273 A1 | 12/2014 | | |
| WO | WO 2015/084802 A1 | 6/2015 | | |
| WO | WO 2015/117040 A1 | 8/2015 | | |
| WO | WO 2015/200541 A1 | 12/2015 | | |
| WO | WO 2018/045109 A1 | 3/2018 | | |
| WO | WO-2019033062 A2 | 2/2019 | | |
| WO | WO-2020102594 A1 | 5/2020 | | |
| WO | WO-2022018055 A1 | 1/2022 | | |
| WO | WO-2022086880 A1 | 4/2022 | | |

OTHER PUBLICATIONS

Frank, D. N., "BARCRAWL and BARTAB: software tools for the design and implementation of barcoded primers for highly multiplexed DNA sequencing". BMC Bioinformatics. Oct. 29, 2009;10:362. doi: 10.1186/1471-2105-10-362.

Hong, L. Z. et al., "BAsE-Seq: a method for obtaining long viral haplotypes from short sequence reads". Genome Biol. 2014;15(11):517. doi: 10.1186/S13059-014-0517-9.

Office Communication dated Nov. 9, 2020 for U.S. Appl. No. 16/253,898.

Office Communication dated Oct. 13, 2020 for U.S. Appl. No. 16/783,301.

Extended European Search Report for European Application No. 17847517.4 dated Apr. 7, 2020.

International Search Report and Written Opinion for International Application No. PCT/SG2014/000172 dated Sep. 24, 2014, 19 pages.

International Search Report and Written Opinion in corresponding PCT Application No. PCT/US2018/046356 dated Feb. 6, 2019, 23 pages.

International Search Report and Written Opinion issued in PCT/US2017/049496 dated Jan. 18, 2018, 1-16.

Supplemental European Search Report issued in EP application No. 18844243 dated Aug. 10, 2021, 2 pages.

[No Author Listed] FASTX-Toolkit. FASTQ/A short-reads pre-processing tools. 2009. Accessed online Aug. 1, 2022 at hannonlab.cshl.edu/fastx_toolkit/, 2 pages.

[No Author Listed] Illumina, CASAVA 1.8.2 Quick Reference Guide, Oct. 2011, [Retrieved on Sep. 23, 2014] Retrieved from the Internet: support.illumina.com/content/dam/illumina-support/documents/myillumina/212b4ea1-8658-4505-9b42-008eb0a8b300/casava_qrg_15011197c.pdf, 28 pages.

Bankevich et al., SPAdes: A New Genome Assembly Algorithm and Its Applications to Single-Cell Sequencing. J Computational Biology, 2012, 19(5):455-477.

Berglund et al., Next-generation Sequencing Technologies and Applications for Human Genetic History and Forensics, Investigative Genetics, 2011, 2(23)1-15.

Bolger, Trimmomatic: A flexible read trimming tool for Illumina NGS data. 2014. USADELLA.org website. Accessed online Aug. 1, 2022 at www.usadellab.org/cms/?page=trimmomatic, 6 pages.

Buffalo, Scythe—A Bayesian adapter trimmer (version 0.994 BETA). 2014. Accessed online Aug. 1, 2022 at github.com/vsbuffalo/scythe, 7 pages.

Costea, P.I., et al., TagGD: Fast and Accurate Software for DNA Tag Generation and Demultiplexing, PloS One, Mar. 2013, 8(3):1-5.

Etter, P.D., et al., Local De Novo Assembly of RAD Paired-end Contigs Using Short Sequencing Reads, PLoS One, Apr. 2011, 6(4):1-10.

Hayashi et al., Highly accurate genome sequences of *Escherichia coli* K-12 strains MG1655W3110, Molecular Systems Biology, 2006, 1-5.

Hwang et al., Single-cell RNA sequencing technologies and bioinformatics pipelines, Experimental & Molecular Medicine, 2018, 50(96):1-14.

Jiang et al. Skewer: a fast and accurate adapter trimmer for next-generation sequencing paired-end reads. BMC Bioinformatics, 2014, 15(182):1-12.

Li et al., SOAP: short oligonucleotide alignment program, Bioinformatics, Mar. 2008, 2(5):713-714.

Lim et al. Directed evolution of nucleotide-based libraries using lambda exonuclease, BioTechniques, Dec. 2012, 53(6):357-364.

(56) References Cited

OTHER PUBLICATIONS

Liu et al., Long Read Alignment Based on Maximal Exact Match Seeds, Bioinformatics, Sep. 2012, 28(18):i318-i324.
Margulies et al., Genome Sequencing in Microfabricated High-density Picolitre Reactors, Nature, Sep. 15, 2005, Published Online: Jul. 31, 2005, 437:(7057):376-380.
Peng et al. Generation of long insert pairs using a Cre-LoxP Inverse PCR approach, PLoS One, Jan. 2012, 7(1):e29437:1-8.
Rothberg et al., An Integrated Semiconductor Device Enabling Non-Optical Genome Sequencing, Nature, DOI: 10.1038/nature10242, Jul. 20, 2011, 475:(7356):348-352.
Rungpragayphan, et al. High-throughput, cloning-independent protein library construction by combining single-molecule DNA amplification with in vitro expression, J Mol Biol. Apr. 26, 2002, 318(2):395-405.
Sambrook et al. (1989) Molecular Cloning: A Laboratory Manual, 2nd Edition. New York, NY: Cold Spring Harbor, N.Y., 1989, 17.37-17.42.
Shendure, J. et al. Accurate multiplex polony sequencing of an evolved bacterial genome. Science, 2005, 309(5741): 1728-1732.
Shiroguchi et al., Digital RNA sequencing minimizes sequence-dependent bias and amplification noise with optimized single-molecule barcodes. PNAS, Jan. 24, 2012, 109(4):1347-1352, and Supporting Information, 14 pages total.
Souza et al. Long-term experimental evolution in *Escherichia coli*. V. Effects of recombination with immigrant genotypes on the rate of bacterial evolution, Journal of Evolutionary Biology, 1997, 10:743-769.
Stapleton et al., A Cell-Free Microtiter Plate Screen for Improved [FeFe] Hydrogenases, PLoS One. May 10, 2010, 5(5):e10554:1-8.
Zerbino et al., Velvet: Algorithms for de novo short read assembly using de Bruijn graphs, Genome Research. May 2008, 18(5):821-829.
Levy, S.E., and Myers, R.M. "Advancements in Next-Generation Sequencing," Annu. Rev. Genom. Hum. Genet., 2016, 17:95-115.
Kanagal-Shamanna R., "Emulsion PCR: Techniques and Applications," Methods Mol. Biol, 2016, 1392:33-42.
Brownie, J. et al. "The elimination of primer-dimer accumulation in PCR," Nucleic Acids Res., Aug. 15, 1997, 25(16):3235-3241.
Ettwiller, L. et al., "A novel enrichment strategy reveals unprecedented number of novel transcription start sites at single base resolution in a model prokaryote and the gut microbiome," BMC Genomics, 2016, 17(199):1-14.
Stapleton, J.A. et al., "Development of an In Vitro Compartmentalization Screen for High-Throughput Directed Evolution of [FeFe] Hydrogenases," PLos ONE, Dec. 2010, 5(12):e15275, 8 pages.
Co-pending U.S. Appl. No. 18/330,279, inventors Stapleton; James A. et al., filed Jun. 6, 2023.
Co-pending U.S. Appl. No. 18/479,717, inventors Quake; Stephen R. et al., filed Oct. 2, 2023.

\* cited by examiner

METHOD FOR GENERATING EXTENDED SEQUENCE READS

CROSS-REFERENCE TO RELATED APPLICATIONS

This application is a national stage filing under 35 U.S.C. § 371 of international application number PCT/SG2014/000172, filed Apr. 17, 2014, which was published under PCT Article 21(2) in English and claims benefit of, and priority from, Singapore patent application number 201302940-0, filed on 17 Apr. 2013, the contents of which are hereby incorporated herein by reference.

FIELD OF THE INVENTION

The present invention relates to a method for generating extended sequence reads and in particular, but not exclusively, to a method for generating extended sequence reads of large genomes.

BACKGROUND

The current maximum read length of next-generation sequencing technologies, such as those developed by Illumina® and Life Technologies™, is around 250 bases. The read length is one of the main factors that determine the quality of a genome assembly. In general, longer reads make better assemblies because they span more repeats.

Furthermore, increasing the read length of next-generation sequencing technologies enables broader applications such as being able to sequence larger genomes, generate extended sequence reads and be useful for long-range haplotype analysis on targeted genomic regions.

Therefore, there is a need for an approach to increase the read length of these commercially available sequencing platforms to several kilobases.

SUMMARY OF THE INVENTION

In accordance with a first aspect of the present invention, there is provided a method for generating extended sequence reads of long DNA molecules in a sample, comprising the steps of:
  (i) assigning a specific barcode sequence to each template DNA molecule in a sample to obtain barcode-tagged molecules;
  (ii) amplifying the barcode-tagged molecules;
  (iii) fragmenting the amplified barcode-tagged molecules to obtain barcode-containing fragments;
  (iv) juxtaposing the barcode-containing fragments to random short segments of the original DNA template molecule during the process of generating a sequencing library to obtain demultiplexed reads; and
  (v) assembling the demultiplexed reads to obtain extended sequence reads for each DNA template molecule.

Preferably, the method further comprises the step of labelling the amplified barcode-tagged molecules with biotin.

Preferably, wherein the step of fragmenting the amplified barcode-tagged molecules comprises the step of subjecting the amplified barcode-tagged molecules to unidirectional deletion from the barcode-distal end of the barcode-tagged molecules to obtain barcode-containing fragments.

Preferably, wherein the step of fragmenting the amplified barcode-tagged molecules comprises the steps of:
  (i) creating a nick at the barcode-distal end of the amplified barcode-tagged molecules;
  (ii) performing a nick translation towards the barcode-proximal end; and
  (iii) treating with endonuclease the resulting molecules to generate blunt ends, to obtain barcode-containing fragments.

Preferably, wherein the step of fragmenting the amplified barcode-tagged molecules comprises the step of performing random fragmentation by a mechanical method or an enzymatic method to obtain barcode-containing fragments.

Preferably, the barcode-containing fragments have lengths ranging from about 300 base pairs to N base pairs, wherein N equals to the length of the original DNA template molecule.

Preferably, the method further comprises the step of purifying the barcode-containing fragments using streptavidin-coated paramagnetic beads.

Preferably, wherein the step of purifying the barcode-containing fragments comprises dissociating the biotin-labelled molecules from the streptavidin-coated paramagnetic beads.

Preferably, wherein the step of purifying the barcode-containing fragments comprises dissociating the biotin-labelled molecules from the streptavidin-coated paramagnetic beads, further comprises the step of circularizing the purified barcode-containing fragments by intramolecular ligation.

Preferably, the method further comprises the step of ligating sequencing adaptors onto the ends of the barcode-containing fragments prior to the step of juxtaposing the barcode-containing fragments to random short segments of the original DNA template molecule.

Preferably, the specific barcode sequence is assigned by linker ligation to each template DNA molecule.

Preferably, wherein the step of amplifying the barcode-tagged molecules is by circularizing the barcode-tagged molecules and performing rolling circle amplification.

Preferably, the extended sequences reads are compatible for sequencing on sequencing platforms.

In accordance with a second aspect of the present invention, there is provided a system for obtaining extended sequence reads from template molecules of a DNA sequence, comprising:
  (i) a quality filtering module for filtering raw paired-end sequence reads from a sequencer by removing read-pairs with low quality scores, removing read-pairs with missing barcode sequences and trimming platform-specific adaptor sequences;
  (ii) a barcode analysis module for identifying highly-represented barcodes and re-assigning sequences associated with poorly-represented barcodes;
  (iii) a demultiplexing module for using barcode sequences as identifiers to obtain reads associated with individual template molecules and removing duplicate read-pairs; and
  (iv) an assembly module for assembling demultiplexed reads to obtain extended sequence reads for each template molecule.

The system in accordance to the second aspect of the present invention wherein the DNA sequence is a known sequence, further comprising:
  (i) a sequence alignment module for performing paired-end alignment to a reference sequence and removing disconcordant alignments;
  (ii) a demultiplexing module for using barcode sequences as identifiers to obtain alignments to individual template molecules and removing duplicate read-pairs in place of the demultiplexing module according to the second aspect of the present invention; and (iii) a haplotyping module for obtaining pileup of aligned reads at each position along the reference sequence, determining consensus base-call at each position and assembling base-calls to obtain extended sequence reads for each template molecule in place of the assembly module according to the second aspect of the present invention.

In accordance with a third aspect of the present invention, there is provided a computer-readable medium with an executable programme stored thereon, the programme comprising instructions for obtaining extended sequence reads from template molecules of a DNA sequence, wherein the programme instructs a microprocessor to perform the following steps:

(i) filtering raw paired-end sequence reads from a sequencer by removing read-pairs with low quality scores, removing read-pairs with missing barcode sequences and trimming platform-specific adaptor sequences;

(ii) identifying highly-represented barcodes and re-assigning sequences associated with poorly-represented barcodes;

(iii) using barcode sequences as identifiers to obtain reads associated with individual template molecules and removing duplicate read-pairs; and (iv) assembling demultiplexed reads to obtain extended sequence reads for each template molecule.

The computer-readable medium in accordance to the third aspect of the present invention wherein the DNA sequence is a known sequence, wherein the programme instructs the microprocessor to further perform the following steps:

(i) performing paired-end alignment to a reference sequence and removing disconcordant alignments at the step of identifying highly-represented barcodes and re-assigning sequences associated with poorly-represented barcodes;

(ii) replacing the step of using barcode sequences as identifiers to obtain reads associated with individual template molecules and removing duplicate read-pairs with the step of using barcode sequences as identifiers to obtain alignments to individual template molecules and removing duplicate read-pairs; and (iii) replacing the step of assembling demultiplexed reads with the step of obtaining pileup of aligned reads at each position along the reference sequence, determining consensus base-call at each position and assembling base-calls to obtain extended sequence reads for each template molecule.

The present invention provides an approach that can: 1) increase the effective read length of these commercially available sequencing platforms to several kilobases and 2) be broadly applied to obtain long sequence reads from mixed template populations.

The present invention applies the concept of barcoding to generate long sequence reads by providing a technical advance in juxtaposing the assigned barcode to random overlapping segments of the original template.

The present invention relies on assigning barcodes to individual template molecules, allowing for unambiguous assembly of template sequences even for molecules with high sequence similarity. This also means that the present invention will work for sequencing targeted genomic regions or viral genomes.

Accordingly, aspect(s) of the present invention also includes: — a) A method to assign unique DNA barcodes, i.e., a random string of DNA nucleotides, to individual long (>3 kilo bases (kb)) template molecules.

b) A method to juxtapose the assigned DNA barcode to random short segments of the original template molecule during the process of generating a sequencing library.

c) A method of using the DNA barcode associated with each molecule of a sequencing library to identify the template of origin.

d) A method of using DNA barcodes to substantially reduce the error rate of massively parallel sequencing.

e) A method for barcode-directed assembly of short sequence reads to obtain individual template sequences.

Other aspects and advantages of the present invention will become apparent to those skilled in the art from a review of the ensuing description, which proceeds with reference to the following illustrative drawings of preferred embodiments.

BRIEF DESCRIPTION OF THE DRAWINGS

Embodiments of the invention will now be described, by way of example only, with reference to the accompanying drawings, in which:

FIG. 1: Barcode assignment and mutation identification. (A) Each template molecule is assigned to a random barcode, which will uniquely identify each template molecule from a heterogeneous sample. Barcodes also perform another function of removing the vast majority of errors introduced by next-generation sequencing. Briefly, barcode assignment primers carrying universal sequences (green rectangle; Uni-A or Uni-B) on their 5'-end will anneal to opposite ends of template. One of the primers will also carry a barcode (blue rectangle). After two rounds of linear amplification, each template molecule will be tagged with a unique barcode. Next, barcode assignment primers are removed by exonuclease digestion, followed by up to 40 cycles of PCR using universal primers to generate whole-genome amplicons. After PCR amplification, mutations that pre-existed on the template (red cross) or errors introduced during barcode assignment cycle #1 or #2 (blue cross) will be found in all molecules associated with a particular barcode (hereafter referred to as "daughter" molecules). In contrast, errors introduced in subsequent steps of library preparation, sequencing, or base-calling (green cross) can be easily identified because they will only be present in a minority of daughter molecules. (B) To generate uniform sequence coverage across each template molecule, each barcode-tagged genome will be subjected to a series of molecular biologic steps that will ultimately ligate sequencing adaptors (red rectangles) onto the ends of overlapping fragments of the genome. The resulting sequence reads will be assigned to the template molecule identified by the barcode.

FIG. 2: Methodology to generate library of overlapping fragments tagged with the same barcode. After PCR amplification with universal primers, the PCR amplicons are subjected to unidirectional deletion from the barcode-distal end to achieve a broad size distribution of fragments ranging from ~300 bp to N bp, where N equals the length of the original template molecule. Barcode-containing fragments are purified using streptavidin-coated paramagnetic beads. Next, the biotinylated DNA is dissociated from the bead/DNA complex and circularized by intramolecular ligation. After circularization, different regions of the template will be juxtaposed to its barcode. The double-stranded DNA circles are subjected to library preparation by adapting a commonly used transposome-based method (Illumina®) to generate molecules that are compatible for sequencing on the Illumina® platform.

FIG. 7: Allele frequency of mixed clones. Two HBV clones with 17 known SNPs between them were mixed at (A) 1:99 or (B) 1:9 ratios prior to barcoding. BAsE-Seq was performed for each mixed-clone pool. Barcodes were removed from each read-pair prior to alignment and the resulting data was treated as a "bulk" sequencing experiment to determine overall allele frequencies at the SNP positions. The allele frequencies in both libraries were very close to the mixing ratio (indicating that pipetting error and PCR bias were negligible), and were used as control libraries to test the sensitivity and accuracy of our methodology.

FIG. 8: Predicted SNV frequencies and background error rate. Single nucleotide variants (SNVs) in Lib_1:99 (control library containing minor haplotype present at 1% frequency) were estimated by calculating the frequency of Clone-1 genotype calls present in 2881 high coverage genome sequences. In this control library containing a minor haplotype present at 1% frequency, true-positive SNVs were significantly separated from background error (p<0.0001).

DETAILED DESCRIPTION

The present invention applies the concept of barcoding to generate long sequence reads by providing a technical advance in juxtaposing the assigned barcode to random overlapping segments of the original template.

The present invention relies on assigning barcodes to individual template molecules, allowing for unambiguous assembly of template sequences even for molecules with high sequence similarity. This also means that the present invention will work for sequencing targeted genomic regions or viral genomes.

Figure 1:
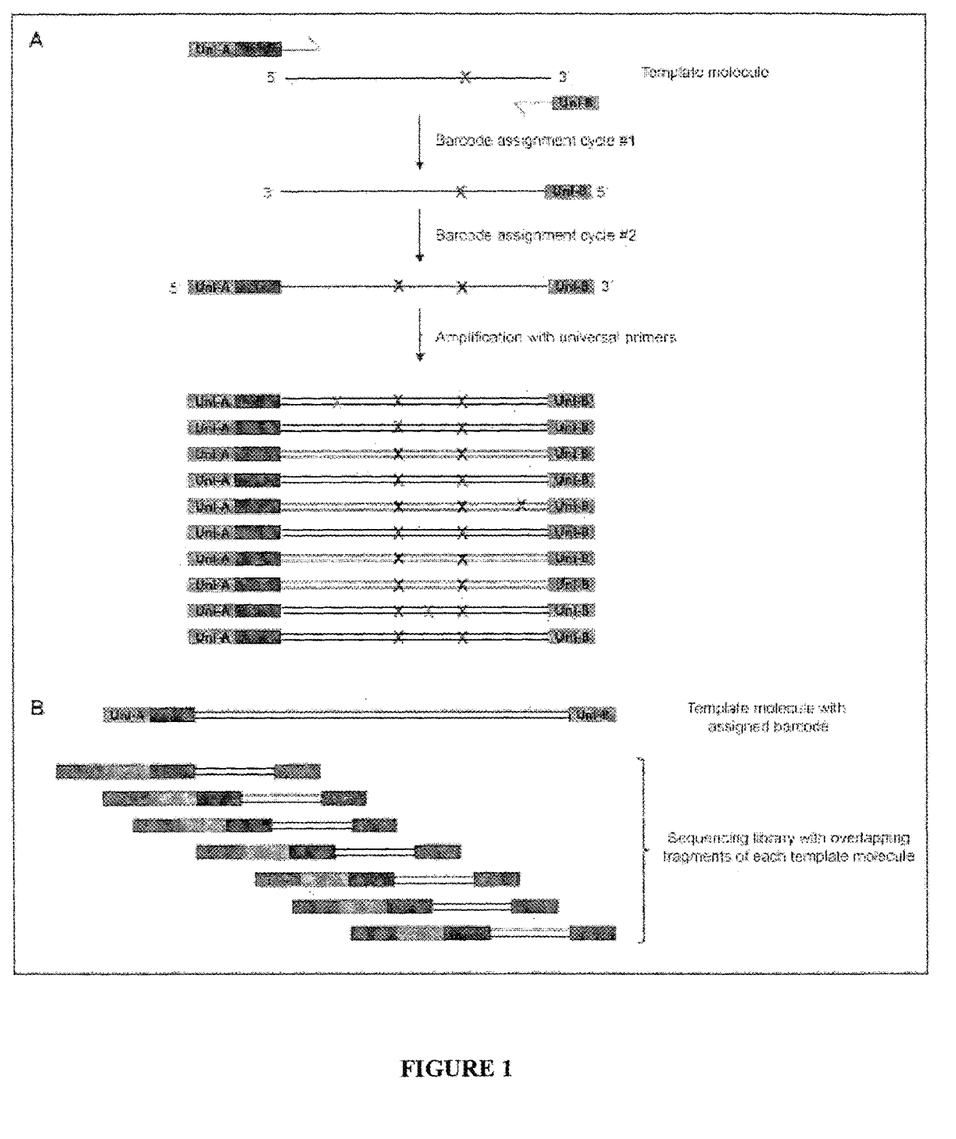
Figure 2:
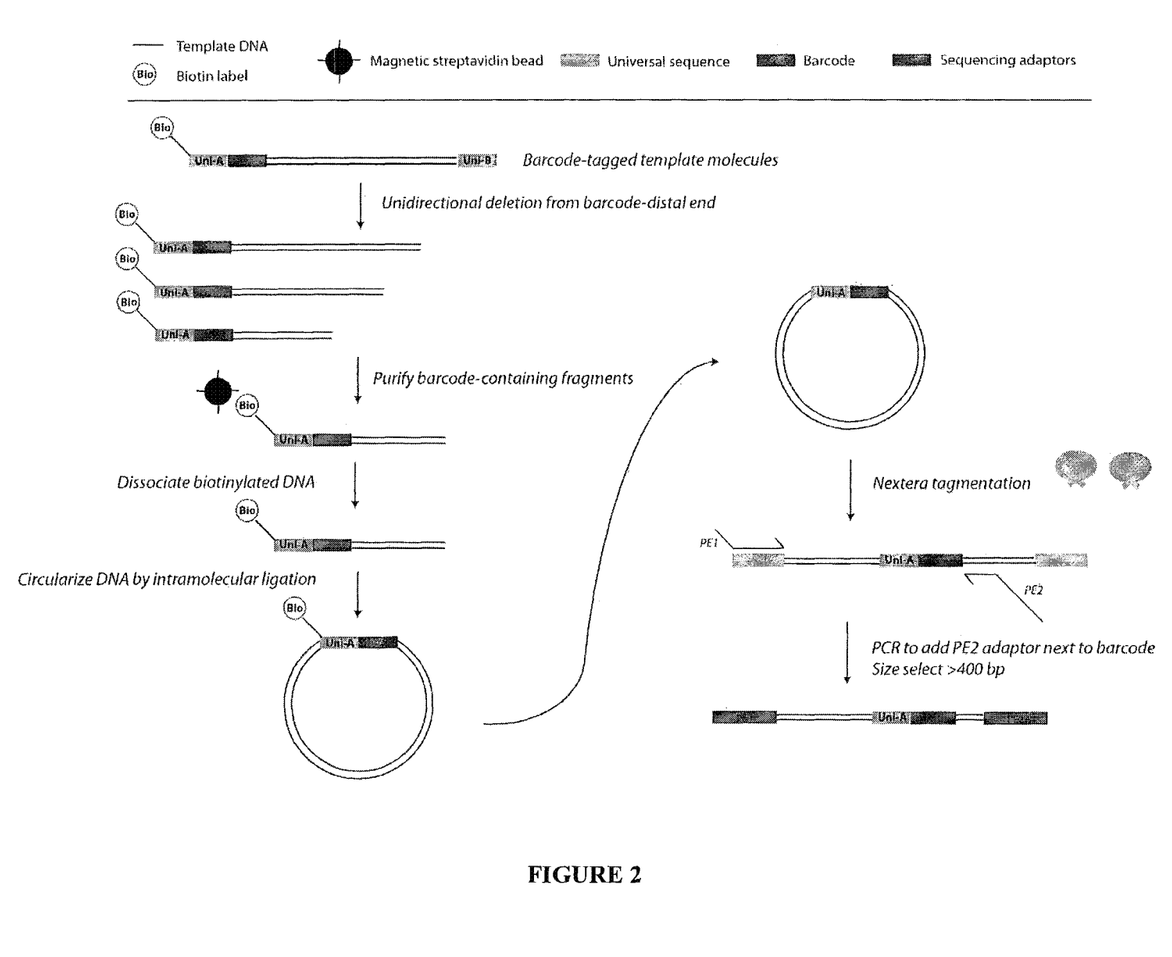

The current maximum read length of next-generation sequencing technologies, such as those developed by Illumina® and Life Technologies™, is around 250 bases. The present invention, also known as "Barcode-directed Assembly for Extra-long Sequences (BAsE-Seq)" provides an approach that can: 1) increase the effective read length of these commercially available sequencing platforms to several kilobases and 2) be broadly applied to obtain long sequence reads from mixed template populations. In brief, our method relies on assigning random DNA barcodes to long template molecules (FIG. 1A), followed by a library preparation protocol that juxtaposes the assigned barcode to random short segments of the original template (FIGS. 1B and 2). The resulting molecules are ligated with platform-specific adaptors for next-generation sequencing. Sequence reads are de-multiplexed using the barcode sequence and used to assemble long-range haplotypes that were present on the original template. In practice, we have applied this technology to perform single virion sequencing on the Hepatitis B virus, a DNA virus with a 3.2 kb genome. In general, we anticipate that this technology can be broadly applied to generate extended sequence reads and will be useful for long-range haplotype analysis on targeted genomic regions, or for improving de novo genome and transcriptome assemblies. A detailed description of our protocol is described in the following paragraphs.

There is described a method for generating extended sequence reads of long DNA molecules (>3 kb), in a sample. The method comprises the steps of: (i) assigning a specific barcode sequence to each template DNA molecule in a sample to obtain barcode-tagged molecules; (ii) amplifying the barcode-tagged molecules; (iii) fragmenting the amplified barcode-tagged molecules to obtain barcode-containing fragments; (iv) juxtaposing the barcode-containing fragments to random short segments of the original DNA template molecule during the process of generating a sequencing library to obtain demultiplexed reads; and (v) assembling the demultiplexed reads to obtain extended sequence reads for each DNA template molecule.

a) Barcode Assignment.

In the first step, individual template molecules are assigned with a unique DNA barcode. In our example, two rounds of PCR amplification are performed using primers with template-specific sequence from opposite ends of the molecule (FIG. 1A). This will generate uniquely tagged template molecules for preparing libraries and can be broadly applied for assigning barcodes to targeted genomic regions. Both primers contain a universal sequence on their 5'-ends and one of them contains a barcode, i.e., a string of 20 random nucleotides (encodes for >$10^{12}$ sequences). To ensure that each template molecule is uniquely assigned, the template should be diluted to obtain a relatively small number of genomes (<$10^9$) compared to unique barcode sequences.

Subsequently, barcode-tagged molecules can be clonally amplified by PCR using universal primers and the PCR product can be used to prepare sequencing libraries. In other manifestations where the template sequence is unknown, the barcode can be assigned by ligation of double- or single-stranded DNA linkers carrying a random string of nucleotides flanked by universal sequences.

The use of unique barcodes to tag individual template molecules has been shown to greatly reduce the error rate of massively parallel sequencing. Using this strategy, mutations that pre-existed on the template and errors introduced during barcode assignment will be found in all daughter molecules.

In contrast, errors introduced in subsequent steps of library preparation, sequencing, or base-calling can be easily removed because they will only be present in a minority of daughter molecules (FIG. 1A). Based on the published error rate of the DNA polymerase used in our protocol, this translates to one error in every 50 template sequences for template molecules that are 3 kb in size. Furthermore, by using barcodes as unique identifiers for individual genomes, sequences associated with each barcode can be assembled into a complete template sequence.

b) Library Preparation.

The goal of library preparation is to tag overlapping fragments of each template molecule with its assigned barcode in order to obtain uniform sequence coverage. This concept is illustrated in FIG. 1B and a detailed outline of the protocol is shown in FIG. 2.

Firstly, clonally amplified barcode-tagged molecules are deleted from the barcode-distal end to achieve a broad size distribution of fragments ranging from ~300 bp to N bp, where N equals the length of the template molecule. Unidirectional deletion can be achieved by protecting the barcode-proximal end with nuclease-resistant nucleotides or a 3'-protruding overhang, and performing time-dependent digestion from the barcode-distal end using a 3' to 5' exonuclease (such as Exonuclease III), followed by treatment with an endonuclease (such as S1 Nuclease or Mung Bean Nuclease) to generate blunt-ends.

Barcode-containing fragments are purified using streptavidin-coated beads, and these biotinylated fragments will be dissociated and subjected to end repair, such that both ends of the molecules are blunt and 5'-phosphorylated. The end-repaired molecules are circularized by intramolecular ligation using a DNA ligase (such as T4 DNA ligase). Uncircularized molecules will be removed by nuclease treatment (such as a combination of Exonuclease I and Lambda Exonuclease).

After circularization, different regions from the original template will be juxtaposed to its barcode. The circularized molecules will be used as template for random fragmentation and adaptor tagging using a transposome-based method, such as the Nextera XT kit (Illumina®).

Importantly, the primers used during PCR enrichment of the sequencing library will be designed such that the second sequencing read will be anchored by the barcode sequence. Thus, this PCR generates double-stranded DNA molecules that are "sequencing-ready". Finally, the PCR products are subjected to size selection before sequencing. A custom sequencing primer that anneals to the forward priming sequence is used for the second sequencing read.

There are several alternative approaches to generate a broad distribution of barcode-tagged molecules before circularization. One approach involves creating a nick at the barcode-distal end using a nicking endonuclease, nick translation towards the barcode-proximal end using DNA polymerase I, followed by treatment with endonuclease to generate a blunt end. Another approach involves performing random fragmentation using a mechanical method, such as using the Covaris instrument for focused-ultrasonication, or an enzymatic method, such as using the NEBNext dsDNA Fragmentase, followed by purification of barcode-containing fragments using streptavidin-coated paramagnetic beads.

An alternative, PCR-free approach to clonal amplification is contemplated, such as circularizing the barcoded template and performing rolling circle amplification using phi29 polymerase.

Barcodes can be assigned by linker ligation. Both linkers will contain universal sequences on their 5'-end to facilitate clonal amplification in the next step. The barcode-containing linker will also contain a unique universal sequence on its 3'-end for primer annealing during the PCR step at the end of the protocol.

Figure 3:
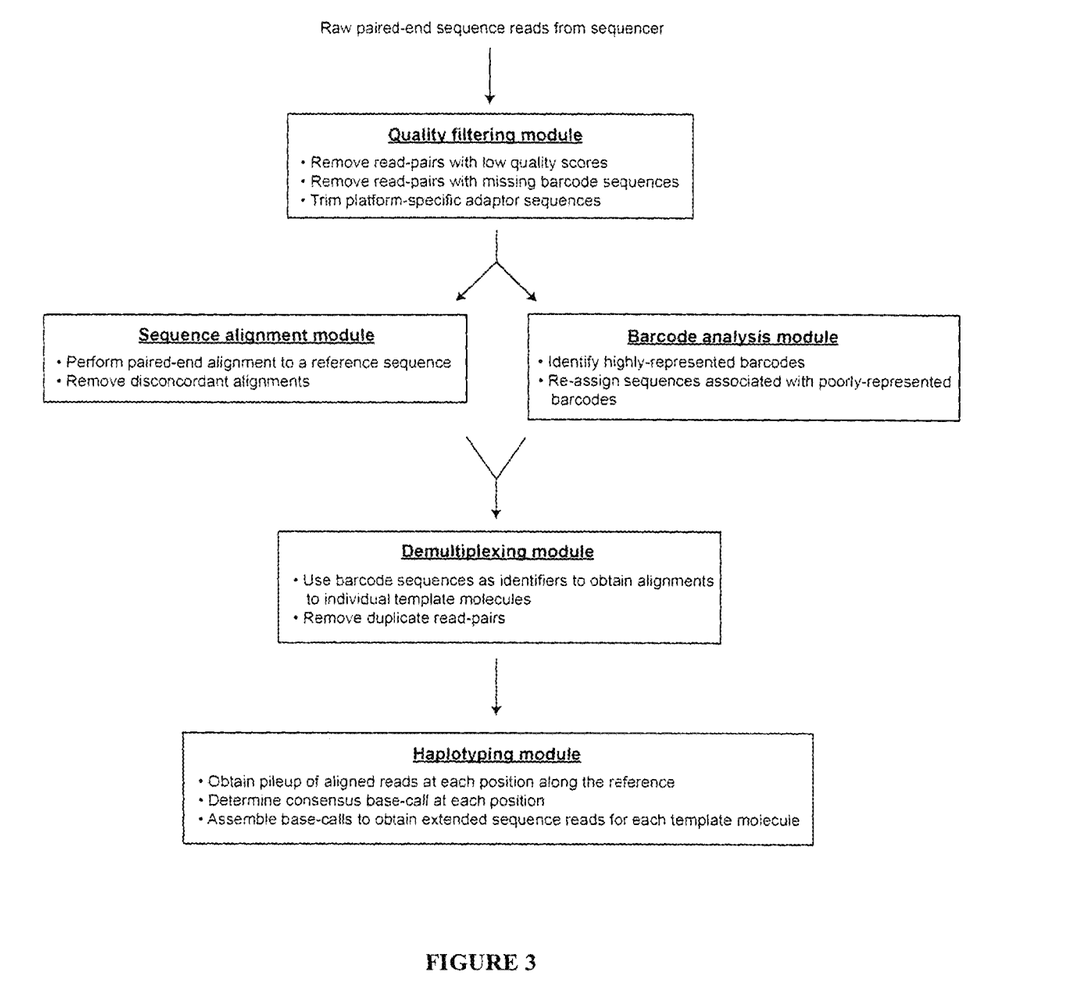
FIG. 3: Software package for obtaining extra-long sequence reads by reference-assisted assembly.
Figure 4:
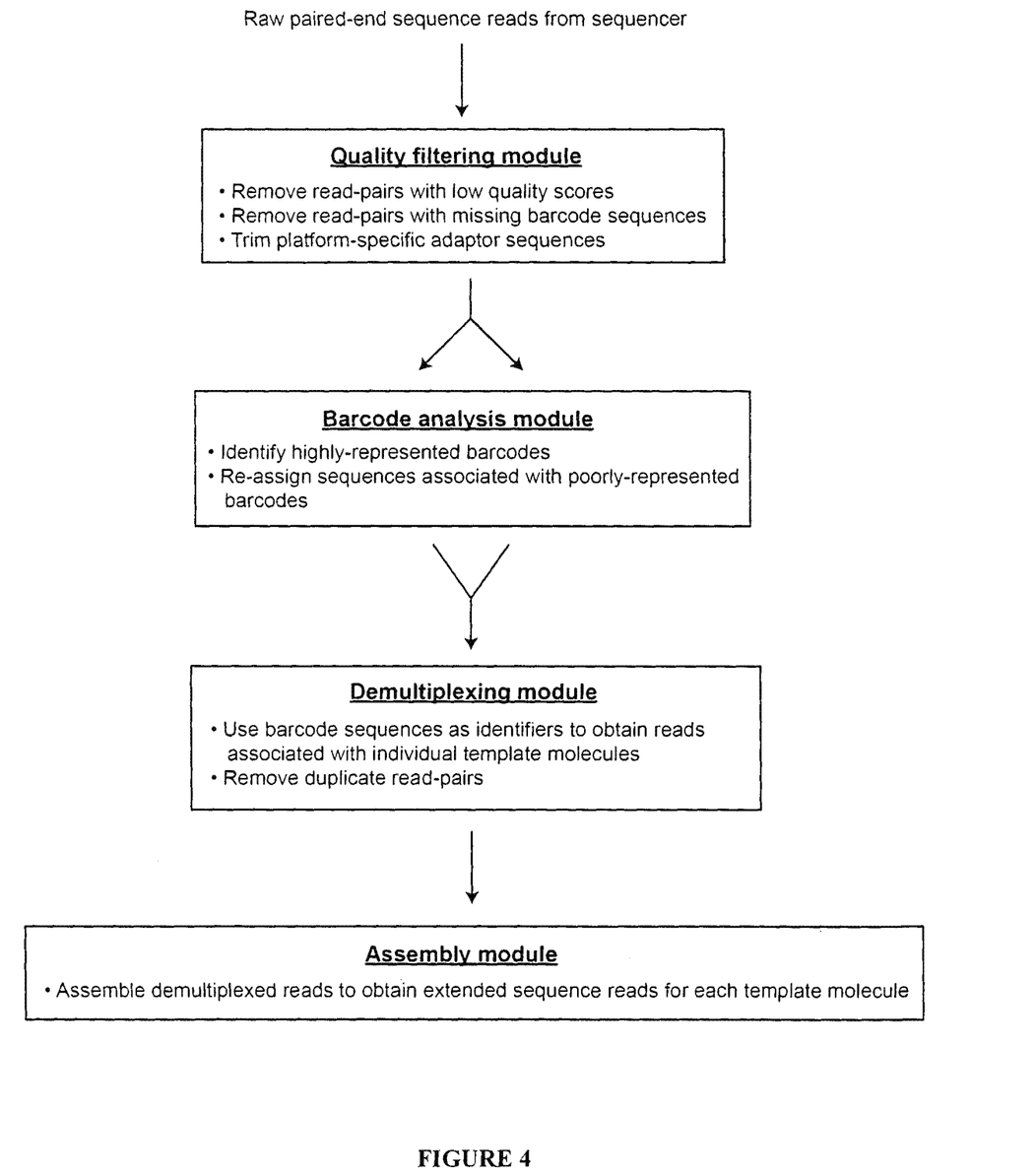
FIG. 4: Software package for obtaining extra-long sequence reads from template molecules of unknown sequence.

Software packages for obtaining extended or extra-long sequence reads by reference-assisted assembly and for obtaining extended or extra-long sequence reads from template molecules of an unknown sequence are illustrated in FIGS. 3 and 4, respectively.

There is described hereinafter a system for obtaining extended sequence reads from template molecules of a DNA sequence. The system comprises (i) a quality filtering module for filtering raw paired-end sequence reads from a sequencer by removing read-pairs with low quality scores, removing read-pairs with missing barcode sequences and trimming platform-specific adaptor sequences; (ii) a barcode analysis module for identifying highly-represented barcodes and re-assigning sequences associated with poorly-represented barcodes; (iii) a demultiplexing module for using barcode sequences as identifiers to obtain reads associated with individual template molecules and removing duplicate read-pairs; and (iv) an assembly module for assembling demultiplexed reads to obtain extended sequence reads for each template molecule (FIG. 4). The template molecules are long, preferably >3 kb.

Where the DNA sequence is a known sequence, the system further comprises (i) a sequence alignment module for performing paired-end alignment to a reference sequence and removing disconcordant alignments; (ii) a demultiplexing module for using barcode sequences as identifiers to obtain alignments to individual template molecules and removing duplicate read-pairs in place of the demultiplexing module shown in FIG. 4; and (iii) a haplotyping module for obtaining pileup of aligned reads at each position along the reference sequence, determining consensus base-call at each position and assembling base-calls to obtain extended sequence reads for each template molecule in place of the assembly module shown in FIG. 4 (FIG. 3).

There is also disclosed a computer-readable medium with an executable programme stored thereon, the programme comprising instructions for obtaining extended sequence reads from template molecules of a DNA sequence, wherein the programme instructs a microprocessor to perform the following steps of (i) filtering raw paired-end sequence reads from a sequencer by removing read-pairs with low quality scores, removing read-pairs with missing barcode sequences and trimming platform-specific adaptor sequences; (ii) identifying highly-represented barcodes and re-assigning sequences associated with poorly-represented barcodes; (iii) using barcode sequences as identifiers to obtain reads associated with individual template molecules and removing duplicate read-pairs; and (iv) assembling demultiplexed reads to obtain extended sequence reads for each template molecule.

Where the DNA sequence is a known sequence, the programme instructs the microprocessor to further perform the following steps of (i) performing paired-end alignment to a reference sequence and removing disconcordant alignments at the step of identifying highly-represented barcodes and re-assigning sequences associated with poorly-represented barcodes; (ii) replacing the step of using barcode sequences as identifiers to obtain reads associated with individual template molecules and removing duplicate read-pairs described above with the step of using barcode sequences as identifiers to obtain alignments to individual template molecules and removing duplicate read-pairs; and (iii) replacing the step of assembling demultiplexed reads described above with the step of obtaining pileup of aligned reads at each position along the reference sequence, determining consensus base-call at each position and assembling base-calls to obtain extended sequence reads for each template molecule.

Examples

Hepatitis B virus (HBV), which contains a 3.2 kb dsDNA genome, was used as a template for methodology development and generating proof-of-concept data. The results presented below demonstrate the use of BAsE-Seq to obtain long (~3.2 kb) sequence reads from individual template molecules, thereby achieving single virion sequencing of HBV.

HBV DNA was isolated from a chronically infected patient, PCR-amplified to obtain full-length viral genomes, and cloned into a TOPO pCR2.1 vector (Life Technologies™). Sanger sequencing was performed across each clone to obtain full-length sequences, and two clones (Clone-1 and Clone-2) with 17 single nucleotide polymorphisms (SNPs) between them were used as input for barcode assignment. In the results presented hereafter, barcode-tagged whole-genome amplicons from 20,000 template molecules (HBV genomes) were used as input for library preparation using the BAsE-Seq protocol described above.

Figure 5:
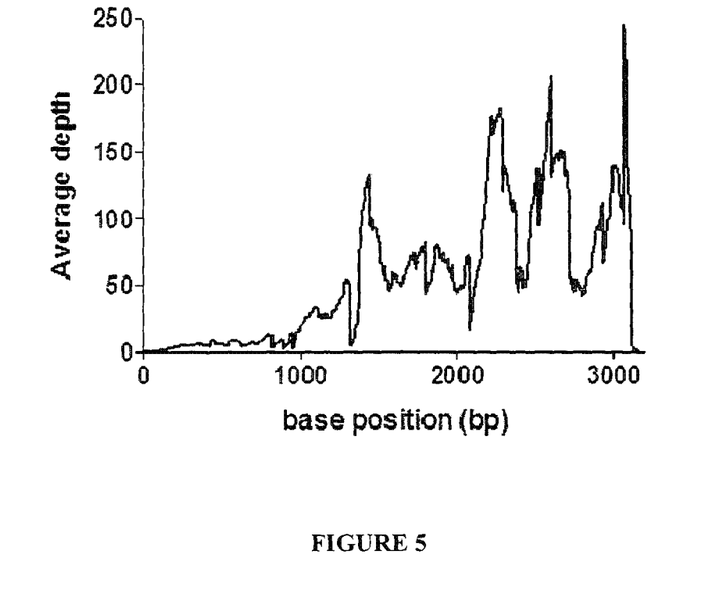
FIG. 5: Average coverage depth per HBV genome. Average coverage depth per base position across the HBV genome. Data shown is the average coverage from 4,294 unique viral genomes.
Figure 6:
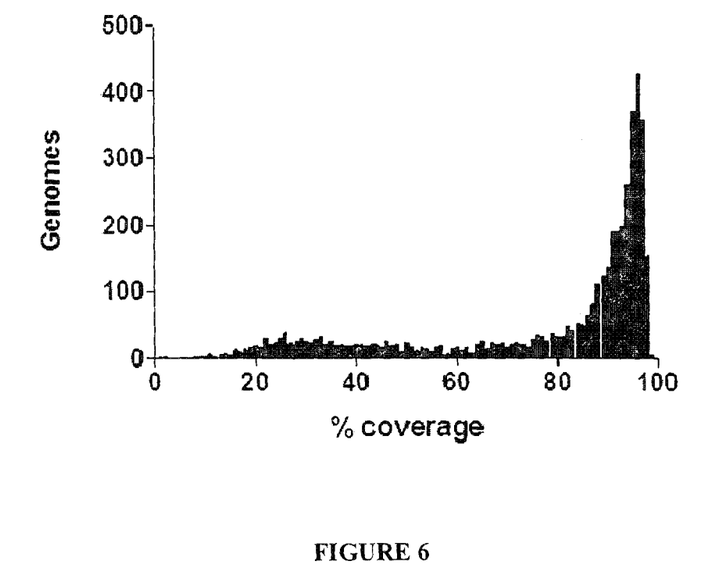
FIG. 6: Genome coverage per HBV genome. Percentage of each genome covered by at least 5 unique reads. 2,717 high coverage genomes—defined as ≥5 reads across ≥85% of the genome—were recovered.

Summary statistics from a typical single virion sequencing experiment of HBV are shown in Table 1, and coverage data per template molecule are illustrated in FIGS. 5 and 6. In this library, 18,143,186 read-pairs were obtained from the MiSeq sequencer (Illumina®), from which Ser. No. 12/004,237 read-pairs contained the barcode in the expected orientation. After trimming for adaptor, barcode tag and universal sequences, and removing reads shorter than 15 bp, 7,336,915 pass-filter read-pairs were used for alignment to a HBV reference genome. From these read-pairs, 97% read-pairs aligned concordantly, and were distributed across 4,294 individual template molecules, 2,717 of which were identified as "high coverage" and were used for constructing long reads.

TABLE 1

Summary statistics from a BAsE-Seq run of HBV.

| | MiSeq run (2 × 150 bp) |
| --- | --- |
| Genomes as input | 20,000 |
| Sequencing read-pairs | 18,143,186 |
| Barcode-associated read-pairs[1] | 12,004,237 (66%) |
| Pass-filter read-pairs[2] | 7,366,915 |
| Concordantly aligned to HBV genome | 7,151,142 (97% of pass-filter) |
| Unique barcodes observed[3] | 4,294 |
| High coverage HBV genomes[4] | 2,717 |

Figure 7:
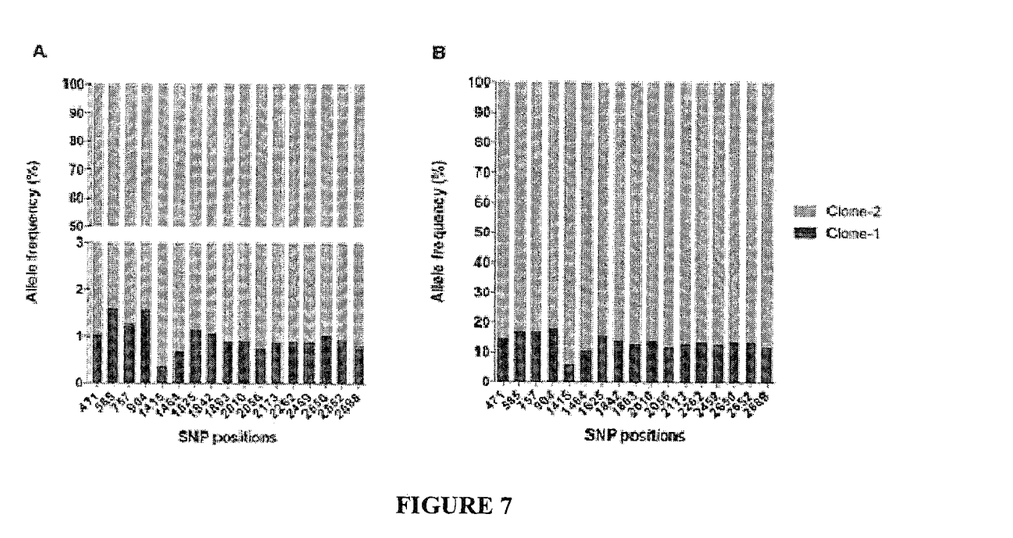
Figure 8:
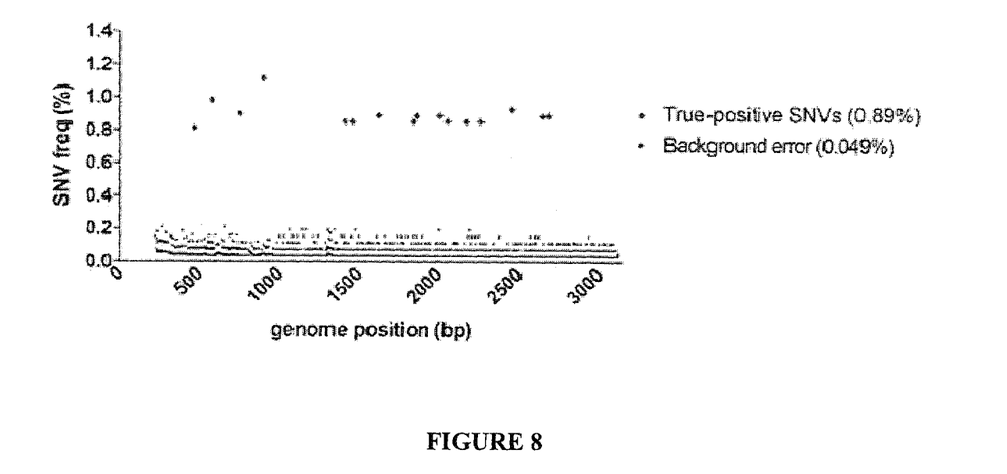

[1]Read-pairs that contain the barcode in the expected orientation
[2]Read-pairs that are ≥15 bp after removal of adaptor and universal sequences
[3]Barcodes associated with at least 50 read-pairs
[4]≥5 unique reads per base position across ≥85% of the genome To test the sensitivity and accuracy of our methodology in generating long sequence reads, Clone-1 and Clone-2 were mixed at different ratios to generate a mixed template population where Clone-1 is present at approximately 1% or 10% frequency in the sample. BAsE-Seq was performed on each mixed-template pool. Firstly, barcodes were removed from each read-pair prior to alignment and the resulting data was treated as a "bulk" sequencing experiment to determine overall allele frequencies at the SNP positions. The minor allele frequencies in both libraries were very close to the mixing ratio—0.98% for the "1% pool" (Lib_1:99) and 13.44% for the "10% pool" (Lib_1:9)—indicating that the mixed template pool was generated correctly and PCR bias was negligible (Table 2 and FIG. 7). Subsequently, the "bulk" sequence data was de-multiplexed using barcode sequences and sequence reads from individual template molecules were analyzed to obtain ~3.2 kb reads. Using the long sequence reads, 17-SNP haplotypes were generated for each template molecule. In Lib_1:9, 240 molecules carried a Clone-1 haplotype and 1,639 molecules carried a Clone-2 haplotype, corresponding to a 12.77% minor haplotype frequency. In Lib_1:99, 20 molecules carried a Clone-1 haplotype and 1,912 molecules carried a Clone-2 haplotype, corresponding to a 1.04% minor haplotype frequency. Importantly, chimeric sequences where Clone-1 and Clone-2 SNPs were found on the same molecule were present at ≤0.1% frequency. Furthermore, the use of barcodes to correct for sequencing errors resulted in a very low error rate for BAsE-Seq, allowing for significant separation of true sequence variants from background noise in Lib_1:99 (Table 2 and FIG. 8).

TABLE 2

Detection of low frequency haplotypes by BAsE-SEq

| | Lib_1:99 | Lib_1:9 |
| --- | --- | --- |
| Mixing ratio (Clone-1 vs. Clone-2) | 1:99 | 10:90 |
| Expected minor clone frequency[1] | 0.98% | 13.44% |
| Observed minor clone haplotypes (Clone-1/Clone-2)[2] | 1.04% (20/1912) | 12.77% (240/1639) |
| Chimeric haplotypes | 0.10% (2/1912) | 0.06% (1/1639) |

[1]Based on average allele frequency of Clone-1 SNPs from "bulk" sequencing analysis
[2]Based on 17-SNP haplotypes observed in the data from individual template molecules Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text, if any, is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (e.g. size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

While the invention has been described with reference to specific methods and embodiments, it will be appreciated that various modifications and changes may be made without departing from the invention.

The invention claimed is:

1. A method comprising:
   (i) assigning a specific barcode sequence to template DNA molecules in a sample, wherein the assigning comprises a polymerase chain reaction (PCR) amplification reaction using primers comprising universal sequences at the 5' ends of the primers, wherein for a template DNA molecule of the template DNA molecules, a primer of the primers additionally comprises a barcode, thereby generating barcode-tagged molecules;
   (ii) clonally amplifying the barcode-tagged molecules, thereby generating amplified barcode-tagged molecules;
   (iii) protecting barcode-proximal ends of the amplified barcode-tagged molecules, thereby generating protected barcode-tagged molecules;
   (iv) fragmenting the protected barcode-tagged molecules to obtain barcode-containing fragments, wherein the fragmenting comprises subjecting the protected barcode-tagged molecules to unidirectional deletion from a barcode-distal end of the protected barcode-tagged molecules;
   (v) circularizing the barcode-containing fragments by intramolecular ligation, thereby juxtaposing a barcode-tagged end of the barcode-containing fragments with a barcode-distal end of the barcode-containing fragments and generating a sequencing library of overlapping fragments;
   (vi) obtaining demultiplexed reads from the sequencing library, wherein demultiplexed reads from the sequencing library comprise sequences of the barcode and the barcode-distal ends of the barcode-containing fragments; and
   (vii) assembling the demultiplexed reads to obtain extended sequence reads for the template DNA molecules.

2. The method of claim 1, further comprising labelling the amplified barcode-tagged molecules with biotin.

3. The method of claim 1, wherein the barcode-containing fragments comprise between about 300 base pairs to N base pairs, wherein N equals a length of one of the template DNA molecules.

4. The method of claim 2, further comprising purifying biotin-labelled barcode-containing fragments using streptavidin-coated paramagnetic beads.

5. The method of claim 4, wherein purifying the biotin-labelled barcode-containing fragments comprises dissociating the biotin-labelled barcode-containing fragments from the streptavidin-coated paramagnetic beads.

6. The method of claim 1, wherein clonally amplifying the barcode-tagged molecules comprises circularizing the barcode-tagged molecules and performing rolling circle amplification.

7. The method of claim 1, wherein the extended sequence reads are compatible for sequencing on a sequencing platform.

8. The method of claim 1, further comprising ligating sequencing adaptors to the barcode-containing fragments prior to the circularizing.

9. The method of claim 1, wherein the template DNA molecules comprise a population of mixed template DNA molecules.

10. The method of claim 1, wherein the sequencing library comprises double-stranded DNA circularized molecules.

11. The method of claim 1, wherein the template DNA molecules have a length of at least 3 kilobases (kb).

12. The method of claim 1, wherein the circularizing is performed by intramolecular ligation using a DNA ligase.

13. The method of claim 6, wherein the rolling circle amplification is performed using a phi29 polymerase.

14. A method comprising:
   (i) assigning a specific barcode sequence to template DNA molecules in a sample, wherein the assigning comprises a polymerase chain reaction (PCR) amplification reaction using primers comprising universal sequences at the 5' ends of the primers, wherein for a template DNA molecule of the template DNA molecules, a primer of the primers additionally comprises a barcode, thereby generating barcode-tagged molecules;
   (ii) clonally amplifying the barcode-tagged molecules, thereby generating amplified barcode-tagged molecules;
   (iii) protecting barcode-proximal ends of the amplified barcode-tagged molecules, thereby generating protected barcode-tagged molecules;
   (iv) fragmenting the protected barcode-tagged molecules to obtain barcode-containing fragments, wherein the fragmenting comprises subjecting the protected barcode-tagged molecules to unidirectional deletion from a barcode-distal end of the protected barcode-tagged molecules;
   (v) circularizing the barcode-containing fragments by intramolecular ligation, thereby juxtaposing a barcode-tagged end of the barcode-containing fragments with a barcode-distal end of the barcode-containing fragments and generating a sequencing library of overlapping fragments;
   (vi) subjecting the sequencing library of overlapping fragments to fragmentation and adaptor tagging via a transposition reaction;
   (vii) obtaining demultiplexed reads from the sequencing library, wherein reads from the sequence library comprise sequences of the barcode and the barcode-distal ends of the barcode-containing fragments; and
   (viii) assembling the demultiplexed reads to obtain extended sequence reads for the template DNA molecules.

15. The method of claim 14, further comprising labelling the amplified barcode-tagged molecules with biotin.

16. The method of claim 14, wherein the barcode-containing fragments comprise between about 300 base pairs to N base pairs, wherein N equals a length of one of the template DNA molecules.

17. The method of claim 15, further comprising purifying biotin-labelled barcode-containing fragments using streptavidin-coated paramagnetic beads.

18. The method of claim 17, wherein purifying the biotin-labelled barcode-containing fragments comprises dissociating the biotin-labelled barcode-containing fragments from the streptavidin-coated paramagnetic beads.

19. The method of claim 14, wherein clonally amplifying the barcode-tagged molecules comprises circularizing the barcode-tagged molecules and performing rolling circle amplification.

20. The method of claim 14, wherein the extended sequence reads are compatible for sequencing on a sequencing platform.

21. The method of claim 14, further comprising ligating sequencing adaptors to the barcode-containing fragments prior to the circularizing.

22. The method of claim 14, wherein the template DNA molecules comprise a population of mixed template DNA molecules.

23. The method of claim 14, wherein the sequencing library comprises double-stranded DNA circularized molecules.

* * * * *